United States Patent [19]

Fuchs et al.

[11] Patent Number: 5,132,431
[45] Date of Patent: Jul. 21, 1992

[54] PROCESS FOR THE CONTINUOUS PREPARATION OF IMIDOPEROXYCARBOXYLIC ACIDS

[75] Inventors: Hermann Fuchs, Königstein; Hanspeter Gethöffer, Frankfurt am Main; Walter Gilb, Hofheim am Taunus, all of Fed. Rep. of Germany

[73] Assignee: Hoechst Aktiengesellschaft, Frankfurt am Main, Fed. Rep. of Germany

[21] Appl. No.: 649,619

[22] Filed: Feb. 1, 1991

[30] Foreign Application Priority Data

Feb. 5, 1990 [DE] Fed. Rep. of Germany ........ 4003309

[51] Int. Cl.$^5$ ................ C07D 209/56; C07D 207/412; C07D 213/69; C07D 207/452
[52] U.S. Cl. ................... 548/473; 540/485; 546/296; 548/545; 548/548; 548/435
[58] Field of Search ............... 548/548, 545, 473, 451; 546/296; 540/485

[56] References Cited

U.S. PATENT DOCUMENTS 4,233,235 11/1980 Camden et al. ...................... 260/502

OTHER PUBLICATIONS

K. T. Nguyen et al, S.I.A./S.P.C.E. Symoposium, "Process Engineering and Chemical Reaction Engineering", Basel, Sep. 12, 1984, p. 45.

*Primary Examiner*—David B. Springer

[57] ABSTRACT

A process for the continuous preparation of imidoperoxycarboxylic acids of the formula

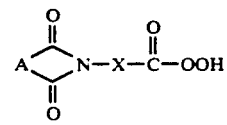

in which
A is $C_2$-$C_4$-alkylene, phenylene, naphthylene or a group of the formula

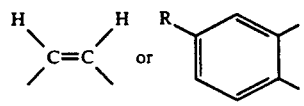

and R is a group of the formula —COOH, —SO$_3$H or —Cl, and
X is $C_1$-$C_{19}$-alkylene or arylene, in which a solution of imidocarboxylic acids of the formula

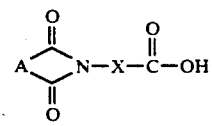

in sulfuric acid or methanesulfonic acid and an aqueous solution of hydrogen peroxide are continuously metered into a static mixer, then the solution of the imidoperoxycarboxylic acid obtained in this way is treated with water and the precipitated product is isolated.

16 Claims, No Drawings

PROCESS FOR THE CONTINUOUS PREPARATION OF IMIDOPEROXYCARBOXYLIC ACIDS

Imidoperoxycarboxylic acids can be employed as oxidants both in organic synthesis (K. Balenkovic et al., J. Chem. Soc, 1962, 3821) and in the bleaching of textiles, as their action takes place even at 60° C. and below (EP 325 290).

In the publications cited above, customary processes corresponding to the prior art are indicated for the preparation of these substances, such as, for example, dissolving or suspending the imidocarboxylic acids in sulfuric acid or methanesulfonic acid and then treating with concentrated aqueous hydrogen peroxide solution with cooling. Owing to the possible risk of explosions, these processes were hitherto not carried out continuously. Continuous processes for the oxidation of carboxylic acids were hitherto only known for aliphatic carboxylic acids, such as acetic acid or 1,12-dodecanedicarboxylic acid.

Thus, U.S. Pat. No. 4,233,235 describes a process for the oxidation of 1,12-dodecanedicarboxylic acid in which the reaction is carried out in a continuously stirred reactor or a recirculation reactor, thorough mixing taking place in the latter case by means of a pump into which the starting materials are fed. One part of the precipitated product is continuously removed from circulation by filtration and the other is fed back into the pump. A means of carrying out the process of this type requires a relatively large outlay in terms of apparatus and control technology and runs the risk of a violent exothermic decomposition of the recycled reaction mixture. Surprisingly, a process has now been found which gives imidoperoxycarboxylic acids in high yield and purity in a simple and continuous procedure and does not have the disadvantages described above.

The invention therefore relates to a process for the continuous preparation of imidoperoxycarboxylic acids of the formula

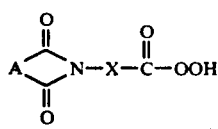

in which

A is $C_2$-$C_4$-alkylene, phenylene, naphthylene or a group of the formula

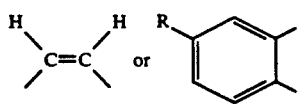

where R is a group of the formula —COOH, —SO$_3$H or —Cl, preferably —COOH and

X is $C_1$-$C_{19}$-alkylene, preferably $C_2$-$C_{11}$-alkylene, or arylene, preferably phenylene, which comprises continuously metering a solution of imidocarboxylic acid of the formula

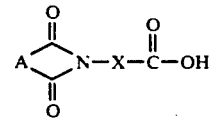

in sulfuric acid or methanesulfonic acid and an aqueous solution of hydrogen peroxide into a static mixer, then treating the solution of the imidoperoxycarboxylic acid obtained in this way with water and isolating the precipitated product. As is known, static mixers contain no stirring components. The liquids are usually thoroughly mixed by swirling in baffles which are arranged in the interior of the mixer.

When carrying out the process, it proved favorable to choose a weight ratio of sulfuric acid or methanesulfonic acid to imidocarboxylic acid of 1–10 to 1, preferably 2–4 to 1. In general, 65–100% strength, preferably 90–98% strength, sulfuric acid is used in order on the one hand to bring the imidocarboxylic acids into solution and on the other hand to protonate the imidocarboxylic acids completely for the oxidation reaction. It is also efficient to carry out the reaction with a molar ratio of hydrogen peroxide (100% strength) to imidocarboxylic acid of 1–4 to 1, preferably 1.5–3 to 1. Commercial aqueous hydrogen peroxide solutions, preferably 35–90% strength preparations, are used for the process according to the invention.

When bringing together the streams of starting materials, care has to be taken that water and sulfuric acid are present in a ratio such that the imidocarboxylic acid or imidoperoxycarboxylic acid does not precipitate and the apparatus becomes blocked. The two solutions of the starting materials are therefore continuously fed from appropriate storage vessels for the reaction and continuously metered into the static mixer. It proved advantageous in this case to connect the lines from the storage vessels to the mixer in a manner such that one pipe runs within the other pipe, i.e. that they are arranged concentrically. In general, the feed rate is 40–100 kg/hour, preferably 50–80 kg/hour, in the case of the imidocarboxylic acid solution and 8–20 kg/hour, preferably 10–16 kg/hour, in the case of the solution of hydrogen peroxide. Both solutions are fed into the mixer simultaneously.

The reaction is carried out in the static mixer without cooling at the temperature produced by the heat of hydration and reaction and is preferably between 60 and 80° C. The mixer comprises a tube having a relatively small volume, as is required for a relatively short residence time of the reaction mixture, preferably of 0.1–10 seconds, in particular 1–3 seconds.

An SMX mixer from Sulzer, for example, is used as the static mixer. The mixer can additionally be equipped with packing materials for a better mixing through of the reactants. However, these packing materials are not absolutely necessary for the process according to the invention.

It also proved particularly advantageous to provide a reaction space for possible afterreactions in direct connection to the mixer and upstream of the outlet. This afterreaction space is normally provided with cooling so that the reaction mixture is cooled to a lower temperature of 30–65° C., preferably 40–60° C. The afterreaction space expediently comprises a tube having a volume of the size that is necessary for a residence time of the reaction mixture of 3–300 seconds, preferably 30–90 seconds.

The reaction mixture is treated with water after leaving the static mixer or afterreaction space by means of a second mixer and the precipitated imidoperoxycarboxylic acid is isolated. It is also possible to pass the reaction mixture into ice-water via an outlet and thus to precipitate the imidoperoxycarboxylic acid. The precipitated imidoperoxycarboxylic acid is customarily filtered off from the reaction mixture, washed until free from mineral acid and dried.

In general, peroxycarboxylic acids can also be stabilized by desensitizing agents. Suitable desensitizing agents are alkali metal, alkaline earth metal or earth metal sulfates or boric acid. These substances can be added after the reaction in amounts of 0 to 80% by weight, relative to the peroxycarboxylic acid, either in solid form or as aqueous solutions or suspensions. It is also possible to only partially neutralize the sulfuric acid by addition of alkali metal hydroxides and to use the resulting alkali metal sulfate as a desensitizing agent (in situ desensitization). If an in situ desensitization was carried out, the washing procedure before drying is unnecessary.

The advantage of the process according to the invention is that the imidocarboxylic acid in concentrated sulfuric acid is mixed in a continuous process without risk with a concentrated hydrogen peroxide solution and can be brought to reaction. The residence time of the reaction components in the mixing apparatus is relatively short here, so no external cooling is necessary. It is convenient to carry out the oxidation reaction of the imidocarboxylic acid with hydrogen peroxide in the mixing apparatus with the heat effect produced by the heat of hydration and reaction. Surprisingly, a complete conversion is in this case ensured without risk within the short contact times.

The imidoperoxycarboxylic acids prepared by the process claimed are in general employed as oxidants in organic synthesis or as bleaching agents in detergent formulations for temperatures below 60° C.

EXAMPLE

Preparation of ε-alimidoperoxycaproic acid 18.75 kg of a solution of 29.7% ε-phthalimidocaproic acid in concentrated sulfuric acid and 3.7 kg of a 50% strength aqueous hydrogen peroxide solution are simultaneously continuously metered into a static tubular mixer ($\phi=15$ mm, $l=80$ mm) at 75 kg/hour and 14.8 kg/hour respectively. The reaction mixture then passes through a tubular afterreaction space ($\phi=15$ mm, $l=3000$ mm) having a cooling water cooling jacket and is then passed into a stirred receiver vessel (100 l kettle made of steel/enamel). The temperature of the reaction mixture is 60° C. at the outlet of the static mixer and is cooled to 40° C. by the external cooling of the afterreaction space. In passing the reaction mixture into the receiver vessel, which is filled with a mixture of 20 kg of water and 20 kg of ice, the ε-phthalimidoperoxycaproic acid precipitates as a solid. The precipitated product is isolated in a filter press (contents 24 l) and washed with water until sulfate-free. After blowing dry for ten hours, 11.5 kg of solid having a water content of 50% (determined by the Karl Fischer method) and an active compound content of 45.4% (corresponds to 91% conversion, determination of the active oxygen content by iodometric titration) are obtained.

We claim:
1. A process for the continuous preparation of an imidoperoxycarboxylic acid of the formula

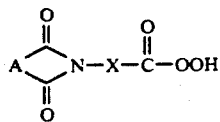

in which
A is $C_2$–$C_4$-alkylene, phenylene, naphthylene or a group of the formula

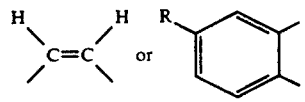

where R is a group of the formula -COOH, -SO$_3$H or -Cl, and
X is $C_1$–$C_{19}$-alkylene, or arylene,
which comprises continuously metering a solution of imidocarboxylic acid of the formula

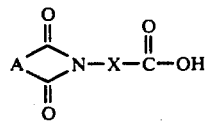

in sulfuric acid or methanesulfonic acid and an aqueous solution of hydrogen peroxide into a static mixer, then treating the solution of the imidoperoxycarboxylic acid obtained in this way with water and isolating the precipitated product.

2. The process as claimed in claim 1, wherein the residence time of the imidocarboxylic acid solution and the hydrogen peroxide solution in the static mixer is 0.1 to 10 seconds.

3. The process as claimed in claim 1, wherein the imidocarboxylic acid solution and the hydrogen peroxide solution are metered into the static mixer via two concentric tubes.

4. The process as claimed in claim 1 wherein the feed rate of the imidocarboxylic acid solution is 40–100 kg/hour and the feed rate of the hydrogen peroxide solution is 8–20 kg/hour.

5. The process as claimed in claim 1 wherein the feed rate of the imidocarboxylic acid is 50–80 kg/hour and the feed rate of the hydrogen peroxide solution is 10–16 kg/hour.

6. The process as claimed in claim 1 wherein the weight ratio of sulfuric acid or methanesulfonic acid to imidocarboxylic acid is 1 to 10:1.

7. The process as claimed in claim 1 wherein the concentration of the sulfuric acid is 65 to 100% by weight.

8. The process as claimed in claim 1 wherein the molar ratio of hydrogen peroxide (100% strength) to imidocarboxylic acid is 1 to 4:1.

9. The process as claimed in claim 1 wherein the reaction is carried out in a static mixer without cooling at a reaction temperature of 60 to 80° C.

10. The process as claimed in claim 1, wherein said process comprises the following steps:
continuously metering said solution of imidocarboxylic acid in sulfuric acid or methenesulfonic acid and said aqueous solution of hydrogen peroxide into the static mixer, thereby forming a reaction mixture the temperature of which is permitted to rise as a result of heat of hydration and heat of reaction, said static mixer having an upstream end and downstream end,
passing said reaction mixture from said downstream end into a coolable afterreaction space, in which the reaction mixture is cooled below the temperature in the static mixer.

11. The process as claimed in claim 10, wherein the reaction mixer is cooled in said afterreaction space to a temperature in the range of 30 to 65° C.

12. The process as claimed in claim 1, wherein said treating of the imidoperoxycarboxylic acid solution with water is carried out in a second mixer or in ice water after the imidopercarboxylic acid solution leaves the static mixer.

13. The process as claimed in claim 10, wherein said treating of the imidopercarboxylic acid solution with water is carried out in a second mixture or in ice water after the imidopercarboxylic acid solution leaves the afterreaction space.

14. The process as claimed in claim 1, wherein the temperature of the reaction mixture in the static mixer resulting from the mixing of said solution of imidocarboxylic acid in sulfuric acid or methanesulfonic acid and said aqueous solution of hydrogen peroxide is permitted to heat up to the temperature produced by the heat of hydration and the heat of reaction.

15. The process as claimed in claim 1, wherein, in said formula, R is a group of the formula —COOH.

16. The process as claimed in claim 1, wherein, in said formula, X is phenylene.

* * * * *

UNITED STATES PATENT AND TRADEMARK OFFICE
CERTIFICATE OF CORRECTION

PATENT NO. : 5,132,431
DATED : July 21, 1992
INVENTOR(S) : Hermann Fuchs, et al

It is certified that error appears in the above-indentified patent and that said Letters Patent is hereby corrected as shown below:

In column 1, at line 11, "(EP 325 290)" should read --(EP 325 289)--.

In claim 13, column 6, at line 11, "mixture" should read --mixer--.

Signed and Sealed this

First Day of March, 1994

*Attest:*

BRUCE LEHMAN

*Attesting Officer*     Commissioner of Patents and Trademarks